United States Patent [19]

Thiele

[11] 4,442,125

[45] Apr. 10, 1984

[54] PROCESS FOR DETACHING OR PREVENTING ATTACHMENT OF MICROORGANISMS TO A SURFACE

[75] Inventor: Geraldine H. Thiele, New Oxford, Pa.

[73] Assignee: Oxford Hill, Ltd., New Oxford, Pa.

[21] Appl. No.: 390,706

[22] Filed: Jun. 21, 1982

Related U.S. Application Data

[63] Continuation-in-part of Ser. No. 918,792, Jun. 26, 1978, Ser. No. 918,795, Jun. 26, 1978, Ser. No. 918,817, Jun. 26, 1978, Ser. No. 927,614, Jul. 24, 1978, Ser. No. 929,119, Jul. 27, 1978, Ser. No. 961,932, Nov. 30, 1978, Ser. No. 724,942, Sep. 20, 1976, abandoned, Ser. No. 724,943, Sep. 20, 1976, abandoned, Ser. No. 113,362, Feb. 8, 1971, Pat. No. 3,741,204, Ser. No. 123,830, Mar. 12, 1971, Pat. No. 3,767,812, Ser. No. 283,662, Aug. 25, 1972, Pat. No. 3,805,776, Ser. No. 369,236, Jun. 12, 1973, Pat. No. 3,924,000, Ser. No. 483,010, Jun. 25, 1974, Pat. No. 3,982,017, Ser. No. 283,663, Aug. 25, 1972, Pat. No. 3,828,772, and a continuation of Ser. No. 755,400, Dec. 29, 1976, Pat. No. 4,097,064, Ser. No. 890,239, Mar. 27, 1978, Ser. No. 642,114, Dec. 18, 1975, abandoned, and a continuation of Ser. No. 153,573, May 27, 1980, abandoned, which is a continuation-in-part of Ser. No. 965,319, Dec. 1, 1978, abandoned, which is a continuation of Ser. No. 890,239, Mar. 27, 1978.

[51] Int. Cl.$^3$ .................. A01N 37/00; A01N 35/02

[52] U.S. Cl. .................. 424/318; 424/343

[58] Field of Search .................. 424/318, 343

[56] References Cited

PUBLICATIONS

Chem. Abst. 63, 955(e), (1965), Velluti et al.
Chem. Abst. 15, 1164(4), (1921), Davis et al.
Chem. Abst. 20, 1457(5), (1926).
J. Bact. 44, 6570(6), (1942), Drea.
Chem. Abst. 45, 7630(d), (1951), Dumoff et al.
Chem. Abst. 28, 2467(5), (1934), Barnes et al.
Chem. Abst. 36, 6570(6), (1942), Drea.

*Primary Examiner*—Douglas W. Robinson
*Attorney, Agent, or Firm*—Fisher, Christen & Sabol

[57] ABSTRACT

Process for preventing microorganisms, such as, mold, fungi, bacteria, and/or virus, from attaching to a surface. The microorganism and/or the surface are treated with an effective amount of a solution. The solution has the property of being antimicrobial. The solution contains an effective amount of a non-necrotic sclerosing fatty acid salt, an effective amount of ethanol, a buffering agent and a water carrier. The fatty acid salt is one prepared from an unsaturated fatty acid having one double bond and from an alkali metal, alkaline earth metal, alkali metal compound or alkaline earth metal compound. The pH of the solution is between 9 and 11.

18 Claims, No Drawings

PROCESS FOR DETACHING OR PREVENTING ATTACHMENT OF MICROORGANISMS TO A SURFACE

This is a continuation of application Ser. No. 153,573, filed on May 27, 1980, now abandoned, which is a continuation-in-part of application Ser. No. 965,319, filed on Dec. 1, 1978, now abandoned, which is a continuation of application Ser. No. 890,239, titled "Injectable Solutions and Processes of Using Such", which was filed on Mar. 27, 1978; this application is a continuation-in-part of application Ser. No. 918,792, titled "Mouthwash and Methods", which was filed on June 26, 1978; this application is a continuation-in-part of application Ser. No. 918,795, titled "Treatment of Sensitive Teeth Syndrome", which was filed on June 26, 1978; this application is a continuation-in-part of application Ser. No. 918,817, titled "Mouthwash and Method for Preventing and Removing Dental Plaque", which was filed on June 26, 1978; this application is a continuation-in-part of application Ser. No. 927,614, titled "Mouthwash and Method for Preventing and Removing Dental Plaque", was filed on July 24, 1978; this application is a continuation-in-part of application Ser. No. 929,119, titled "Mouthwash and Method For Preventing and Removing Dental Plaque", which was filed on July ¢, 1978; this application is a continuation-in-part of application Ser. No. 961,932, titled "Retardation of the Putrefaction of Hides and Skins", which was filed on Nov. 30, 1978; this application is a continuation of application Ser. No. 755,400, which was filed on Dec. 29, 1976, now U.S. Pat. No. 4,097,064, is a continuation-in-part of application Ser. No. 890,239, which was filed on Mar. 27, 1978, is a continuation of application Ser. No. 642,114, which was filed on Dec. 18, 1975, now abandoned, is a continuation-in-part of application Ser. No. 724,942, now abandoned which was filed on Sept. 20, 1976, is a continuation-in-part of application Ser. No. 724,943, which was filed on Sept. 20, 1976, now abandoned, is a continuation-in-part of application Ser. No. 113,362, which was filed on Feb. 8, 1971, now U.S. Pat. No. 3,741,204, is a continuation-in-part of application Ser. No. 123,830, which was filed on Mar. 12, 1971, now U.S. Pat. No. 3,767,812, is a continuation-in-part of application Ser. No. 283,662, which was filed on Aug. 25, 1972, now U.S. Pat. No. 3,805,776, which is a continuation-in-part of application Ser. No. 283,663, which was filed on Aug. 25, 1972, now U.S. Pat. No. 3,828,772, is a continuation-in-part of application Ser. No. 369,236, which was filed on June 12, 1973, now U.S. Pat. No. 3,924,000, and is a continuation-in-part of application Ser. No. 483,010, which was filed on June 25, 1974, now U.S. Pat. No. 3,982,017; application Ser. No. 890,239, is a continuation of application Ser. No. 724,943, is a continuation of application Ser. No. 483,010, is a continuation-in-part of application Ser. No. 369,236, is a continuation-in-part of application Ser. No. 283,662, is a continuation-in-part of application Ser. No. 283,663, is a continuation-in-part of application Ser. No. 123,830, and is a continuation-in-part of application Ser. No. 113,362; application Ser. No. 755,400 is a continuation of application Ser. No. 642,114, is a continuation-in-part of application Ser. No. 483,010, is a continuation-in-part of application Ser. No. 369,236, is a continuation-in-part of application Ser. No. 283,662, is a continuation-in-part of Ser. No. 283,663, is a continuation-in-part of application Ser. No. 123,830, and in a continuation-in-part of application Ser. No. 113,362, application Ser. No. 724,943 is a continuation of application Ser. No. 483,010, is a continuation-in-part of application Ser. No. 369,236, is a continuation-in-part of application Ser. No. 283,662, is a continuation-in-part of application Ser. No. 123,830 and is a continuation-in-part of application Ser. No. 113,362; application Ser. No. 724,942 is a continuation-in-part of application Ser. No. 483,010, is a continuation-in-part of application Ser. No. 369,236, is a continuation-in-part of application Ser. No. 283,663, is a continuation-in-part of application Ser. No. 282,662, is a continuation-in-part of application Ser. No. 123,830, and is a continuation-in-part of application Ser. No. 113,362; application Ser. No. 642,114 is a continuation-in-part of application Ser. No. 483,010, is a continuation-in-part of application Ser. No. 369,236, is a continuation-in-part of application Ser. No. 283,663, is a continuation-in-part of application Ser. No. 283,662, is a continuation-in-part of application Ser. No. 123,830 and is a continuation-in-part of application Ser. No. 113,362; application Ser. No. 483,010 is a continuation-in-part of application Ser. No. 369,236, is continuation-in-part of application Ser. No. 283,663, is a continuation-in-part of application Ser. No. 283,662, is a continuation-in-part of application Ser. No. 123,830, and is a continuation-in-part of application Ser. No. 113,362; application Ser. No. 369,236 is a continuation-in-part of application Ser. No. 283,663, is a continuation-in-part Ser. No. 283,662, is a continuation-in-part of Ser. No. 123,830 and is a continuation-in-part of application Ser. No. 113,362; application Ser. No. 283,663 is a continuation-in-part of application Ser. No. 123,830 and is a continuation-in-part application Ser. No. 113,362; application Ser. No. 283,662 is a continuation-in-part of application Ser. No. 123,830 and is a continuation-in-part of application Ser. No. 113,362; and application Ser. No. 123,830 is a continuation-in-part of application Ser. No. 113,362.

BACKGROUND OF THIS INVENTION

1. Field of This Invention

This invention relates to a process for preventing microbes from adhering to surfaces. This invention also relates to a process for detaching microbes from a surface.

2. Various Considerations

Some believe that bacteria attach or adhere to each other and to animal-cell or inert surfaces by means of a glycocalyx of fibers. Such feltlike glycocalyx are a mass of tangled fibers of polysaccharides, or branching sugar molecules, which extend from the bacterial surface. The adhesion mediated by the glycocalyx determines particular locations of bacteria in natural environments, hence such is a major deterrent in the initiation and progression of bacterial diseases. There is specificity of adherence with some species of bacteria.

Algae have polysaccharide fibers similar to those of bacteria.

One theory is that cells can be made to adhere very rapidly to any surface carrying a positive charge by means of coulombic attractions. Certain environmental enzymes, and enzymes from damaged or dead tissues, plus from inflammatory cells, inhibit cell adhesion either directly or indirectly. Some believe cell detachment is affected by physiologic and pathologic events in the cells in question, and in cells near to them. Various metabolic inhibitors apparently facilitate to a degree cell detachment from a surface. Chlorhexidine apparently facilitates cell detachment.

The distinct phenomenon of cell detachment is not simply the reverse of cell adhesion.

BROAD DESCRIPTION OF THIS INVENTION

An object of this invention is to provide a process for preventing and/or retarding microbes from attaching or reattaching to surfaces. Another object of this invention is to provide a process for detaching microbes attached to a surface. Other objects and advantages of this invention are set out herein or are obvious herefrom to one ordinarily skilled in the art.

The objects and advantages of this invention are achieved by the process of this invention.

This invention involves a process for preventing microorganisms, such as, mold, fungi, bacteria, and/or virus, from attaching or reattaching to a surface. The process includes treating the microorganism and/or the surface with an effective amount of a liquefied composition. The liquefied composition has antimicrobial properties. The liquefied composition consists essentially of an effective amount of a non-necrotic sclerosing fatty acid salt, an effective amount of ethyl alcohol, a buffering agent and a water carrier. The salt is prepared from an unsaturated fatty acid having one double bond and from an alkali metal, alkaline earth metal, alkali metal compound or alkaline earth metal compound. The liquefied composition has a pH between 9 and 11. (Besides microorganisms the process is also effective re algae).

This invention further involves a process for detaching (i.e., interupting and ending the attachment of) microorganisms, such as, mold, fungi, bacteria and/or virus, to a surface. The process includes treating the surface and/or the bacteria attached to the surface with an effective amount of a liquefied composition. The liquefied composition has antimicrobial properties. The liquefied composition consists essentially of an effective amount of a non-necrotic sclerosing fatty acid salt, an effective amount of ethyl alcohol, a buffering agent and a water carrier. The salt is prepared from an unsaturated fatty acid having one double bond and from an alkali metal, alkaline earth metal, alkali metal compound, or alkaline earth metal compound. The liquefied composition has a pH between 9 and 11. (Besides microorganisms the process is also effective re algae.)

The most preferred liquefied composition contains 5 percent of sodium oleate, 5 percent of ethanol, enough disodium hydrogen phosphate to adjust the pH to about 9.8, and the remainder water.

An advantage of the composition used in this invention is that it is nontoxic, and prolonged usage does not show any toxic effects or tissue damage. The composition is easily applied and is rapid in action. The process of this invention is consistently effective. The treatment can be repeated for long term effectiveness.

Preferably the liquefied compositions used in the process of this invention are bottled and stored in dark (amber) glass containers. Plastic bottles tend to deactivate the double bond of the unsaturated fatty acid compound. The result is a lowering of the effectiveness of the process of this invention.

DETAILED DESCRIPTION OF THIS INVENTION

The buffered pH level of the liquefied composition of this invention, re its antimicrobial properties, is believed to be critical.

One theoretical explanation of the broad spectrum of antimicrobial applications of the liquefied compositions of this invention is in essence apparently its cationic and/or chemotactic ability to react or act upon the surface of all cells which have become polarized as a result of injuries, traumas, burns, toxins or infections (bacterial, viral, mold and/or fungal). In a one broad sense the action of the liquefied composition of this invention is akin to a surfactant action inasmuch as it alters the energy relations at interfaces. Essentially only the cationic surface-active agents are employed in medicine and, although they have been proven useful, their serious short-comings have led researchers to believe there is little reason to use the cationic surfactants as antiseptics. Their activity is antigonized by soaps, tissue constituents and pus; when applied to skin they tend to form a film under which bacteria may remain viable; they do not kill spores; their action is slow when compared to that of iodine; they interact with keratin and cause epidermal damage, although that is minor except during continued use, as with certain deodorant preparations and diaper washes. In aggregate the disadvantages would appear greatly to outweigh the advantages.

The innovation of the liquefied composition used in this invention negates the disadvantages of the now available cationic surface-active agents and also complements the advantages which are relatively nonirrating to tissue in effective concentrations and have a rapid onset of action.

The advantages of the liquefied compositions used in this invention as opposed to the contemporaneously available surface-active agents include:

(1) The liquefied composition leaves no residue of toxic metals.

(2) The liquefied composition is non-toxic. (The ingredients of the preferred formulations are on the GRAS list, and are accepted by the FDA for both internal and external use.)

(3) The action is theorized to be motivated by the frH+ and is apparently one of a lifting or depolarizing mechanism.

(4) It stimulates the infiltration of cellular blood components that subsequently differentitate into fibrous and/or fibrocartilagenous tissue.

(5) Does not leave a film under which bacteria may remain viable.

(6) The anti-bacterial action is effective against a wide spectrum of both gram-negative and gram-positive bacteria.

(7) It negates and retards the overgrowth of fungi, mold and yeast.

(8) It is biodegradable.

The liquefied composition of this invention does not enter (other than perhaps the immediate surfaces) the host cells or the invading bacterial cells. So this invention does not have two common problems of antibiotic therapy, namely, toxicity to host cells and the induction of bacterial resistance based on changes in the permeability of the bacterial-cell membrane.

The microbes cannot become immune or resistant to the treatment of this invention. The mode of action of this invention is not systemic. The mode of action is universal in nature so that the overgrowth of one species is prevented.

Adhesion has a central role in the success of pathogenic bacteria, so the prevention of such adhesion is an effective way to prevent or combat infection.

Where microbes have become attached to a surface, this invention can be used to detach them from the surface. Once a microbe has penetrated into the surface of living tissue, it is extremely difficult to detach it.

There is apparently surfactant action, but the key is the critical buffered pH utilizing a unique combination of synergistic components. Attachment and proliferation are prevented or significantly retarded.

The effect of this invention is apparently on all types of solid or semi-solid surfaces, such as, glass, stone, wood, metal plastic, fabrics, gauze, animal or human tissue, vegetable matter and the like.

The process of this invention is effective against microbes, such as, mold, fungi, yeast, bacteria (gram-negative and gram-positive) and virus. The nature of the invention is broad spectru in action and scope. Its action is independent of the immune system, per se.

The liquefied composition of this invention apparently renders various microorganisms, e.g., Streptococci, non-pathogenic apparently by an electrolytic type of action. The microorganisms are prevented from becoming polarized in massive groupings—the liquid composition causes a dispersion of the microorganisms in the body fluids, which keeps them from becoming pathogenic. The mechanism may be that the liquid composition prevents or inhibits the microorganisms from producing toxins. The microorganism are prevented from becoming morbidly pathogenic.

The liquid composition of this invention is not systemic acting, and is not bacteriostatic or bacteracidal or antibacterial or the like, in the normal sense of such terms. The liquid composition apparently keeps the microorganisms from attaching (or brings about a reduction in the microorganisms population).

Where the virulence of a particular bacteria is enhanced by the presence of a nutrient, such as, potassium or magnesium ions, the fatty acid salt can be tailored so that the positive charged moiety is different from such enhancing nutrient. For example, if the enhancing nutrient is sodium, the potassium or lithium salt of the fatty acid could be used in the liquefied composition used in this invention.

The term liquefied compostion includes slurries, suspensions, solutions, pastes, emulsions, etc.

All of the components of the liquefied composition must be and are substantially non-toxic in the amounts and under the conditions of use. The useful (sclerosing) fatty acid compounds must be non-necrotic in effect or operation and must not cause the pathologic death of one or more cells, or a portion of any tissue or any organ (of, say, a plant worker) resulting from irreversible damage to the nucleus.

The pH of the liquefied composition should be between about 9 and about 11, preferably between about 9.5 and about 10.5, and most preferably about 9.8. Each non-necrotic (sclerosing) unsaturated fatty acid compound will produce a different pH at a different concentration levels, so non-toxic agents may be added to adjust the pH level, e.g., sodium dihydrogen phosphate, hydrogen disodium phosphate and/or sodium hydroxide, can be used when sodium oleate or another non-necrotic (sclerosing) unsaturated fatty acid compound is used.

It should be noted that aqueous solutions of alkali metal salts of fatty acids in general have an alkaline or neutral pH. For example, sodium oleate has an alkaline pH—this is usually due to hydrolysis in the aqueous solution.

The most preferred unsaturated fatty acids have eighteen carbon atoms with one double bond in the middle of the chain. The most preferred of such fatty acids is oleic acid (i.e., cis-9-oleic acid or cis-9-octadecenoic acid). The next preferred of such fatty acids is elaidic acid (i.e., trans-9-octadecenoic acid).

Examples of other unsaturated fatty acids having one double bond (i.e., monoethenoid fatty acids) having eighteen carbon atoms are: 2-octadecenoic acid (cis and trans forms). $CH_3(CH_2)_{14}CH=CHCOOH$; 3-octadecenoic acid, $CH_3(CH_2)_{13}CH=CHCH_2COOH$; 4-octadecenoic acid, $CH_3(CH_2)_{12}CH=CH(CH_2)_2COOH$; 5-octadecenoic acid, $CH_3(CH_2)_{11}CH=CH(CH_2)_3COOH$; 6-octadecenoic acid (cis and trans forms), $CH_3(CH_2)_{10}CH=CH(CH_2)_4COOH$; 7-octadecenoic acid (cis and trans forms), $CH_3(CH_2)_9CH=CH(CH_2)_5COOH$; 8-octadecenoic acid (cis and trans forms); 10-octadecenoic acid (cis and trans form), $CH_3(CH_2)_6CH=CH(CH_2)_8COOH$; 11-octadecenoic acid (cis and trans form), $CH_3(CH_2)_5CH=CH(CH_2)_9COOH$; 12-octadecenoic acid (cis and trans form), $CH_3(CH_2)_4CH=CH(CH_2)_{10}COOH$; 15-octadecenoic acid (trans form), $CH_3CH_2CH=CH(CH_2)_{13}COOH$; 16-octadecenoic acid (trans form), $CH_3CH=CH(CH_2)_{13}CH_2COOH$; and 17-octadecenoic acid, $CH_2=CH(CH_2)_{14}CH_2COOH$. (It is believed that the fatty acids having the unsaturation at one end of the hydrocarbon chain, or not in the center thereof, have some undesirable properties and effects in the process of this invention—such compounds are useful, but are certainly much less preferred in result.)

Examples of other useful monoethenoid fatty acids are: 2-tridecenoic acid; 11-tridecenoic acid; 12-tridecenoic acid; 2-dodecenoic acid; 5-dodecenoic acid; 6-dodecenoic acid; 7-dodecenoic acid; 9-dodecenoic acid; 10-dodecenoic acid; 11-dodecenoic acid; 9-eicosenoic acid, $CH_3(CH_2)_9CH=CH(CH_2)_7COOH$; 11-eicosenoic acid; 14-eicosenoic acid; 2-undecenoic acid; 6-undecenoic acid; 9-undecenoic acid; 10-undecenoic acid; 2-decenoic acid; 3-decenoic acid; 4-decenoic acid; 8-decenoic acid; 9-decenoic acid; acrylic acid, $CH_2=CHCOOH$; β-methylacrylic acid (cis and trans forms), $CH_3CH=CHCOOH$; α-methylacrylic acid, $CH_2=C(CH_3)COOH$; vinyl acetic acid, $CH_2=CHCH_2COOH$; β,β-dimethylacrylic acid, $(CH_3)_2C=CHCOOH$; β-pentenoic acid, $CH_3CH=CHCH_2COOH$; allylacetic acid, $CH_2=CHCH_2CH_2COOH$; angelic acid; $CH_3CH=C(CH_3)COOH$ (cis form); tiglic acid, $CH_3CH=C(CH_3)COOH$ (trans form); 2-heptadecenoic acid, $CH_3(CH_2)_{12}CH_2CH=CHCOOH$; 9-heptadecenoic acid (cis and trans forms), $CH_3(CH_2)_6CH=CH(CH_2)_7COOH$; 2-hexadecenoic acid, $CH_3(CH_2)_{12}CH=CHCOOH$; 9-hexadecenoic acid (cis form); 2-tetradecenoic acid; 4-tetradecenoic acid; 5-tetradecenoic acid; 8-tetradecenoic acid; 9-tetradecenoic acid; 2-nonenoic acid; 3-nonenoic acid; 8-nonenoic acid; 2-octenoic acid; 3-octenoic acid; 7-octenoic acid; 2-heptenoic acid; 3-heptenoic acid; 4-heptenoic acid; 5-hetpenoic acid; 6-heptenoic acid; 2-hexenoic acid; 3-hexenoic acid; 4-hexenoic acid; 5-hexenoic acid; 15-tetracosenoic acid; 17-hexacosenic acid and 21-triacentenoic acid.

Examples of fatty acids having a triple bond are: 2-nonynoic acid, $CH_3(CH_2)_5C\equiv CCOOH$; 3-nonynoic acid; 4-nonynoic acid; 5-nonynoic acid; 6-nonynoic acid; 7-nonynoic acid; and 8-nonynoic acid.

Examples of diethenoid fatty acids having eighteen carbon atoms are: 6:8-octadecadienoic acid, $CH_3(CH_2)_8CH=CHCH=CH(CH_2)_4COOH$; 8:10-octadecadienoic acid, (8-trans and 10-trans forms); 8:11-octadecadienoic acid, (8-cis and 11-cis forms); 9:11 octadecadienoic acid, (9-cis, 11-cis and 11-trans forms); 5:12-octadecadienoic acid, (5-cis, 5-trans, 12-trans and 12-cis forms); 9:12-octadecadienoic acid, (9-cis, 9-trans, 12-trans and 12-cis forms); 10:12-octadecadienoic acid, (10-cis, 10-trans, 12-cis and 12-trans forms); 10:13-octadecadienoic acid, (10-cis and 13-cis forms); and 11:14-octadecadienoic acid, (11-cis and 14-cis forms).

Examples of other useful diethenoid acids are:

β-vinylacrylic acid, $CH_2=CHCH=CHCOOH$; sorbic acid, $CH_3CH=CHCH=CHCOOH$; and geranic acid, $(CH_3)_2C=CH(CH_2)_2C(CH_3)=CHCOOH$.

Examples of tetra-triethenoid fatty acid having eighteen carbon atoms are: 9:11:13:15-octadecatetrainoic acid, $CH_3CH_2(CH_2=CH_2)_4(CH_2)_7COOH$; 6:9:12:15-octadecatetraenoic acid; 5:9:12-octadecatrienoic acid (5-trans, 9-cis and 12-cis forms); $CH_3(CH_2)_4CH=CHCH_2CH=CH(CH_2)_2CH=CH(CH_2)_3COOH$; 6:9:12-octadecatrienoic acid; 6:10:14-octadecatrienoic acid; 8:10:12-octadecatrienoic acid (8-cis, 10-trans and 12-cis forms); 9:11:13-octadecatrienoic acid (9-cis, 11-trans, and 13-trans forms); 9:12:15-octadecatrienoic acid (9-cis, 9-trans, 12-cis, 12-trans, 15-cis and 15-trans forms); and 10:12:14-octadecatrienoic acid (10-trans, 12-trans and 14-trans forms). An example of another useful triethenoid fatty acid is dehydrogeranic acid, $(CH_3)_2C=CHCH=CHC(CH_3)=CHCOOH$.

Examples of fatty acids having four double bonds are clupandoic acid, arachidonic acid, α-parinaric acid and β-parinaric acid.

The useful unsaturated fatty acids can contain between 1 and 50 carbon atoms, preferably between 14 and 22 carbon atoms and most preferably by a wide margin have 18 carbon atoms.

Examples of useful unsaturated fatty acids are oleic acid, licanic acid, eleostearic acid and clupanodonic acid. The useful unsaturated fatty acids can be those containing one double bond, e.g., oleic acid, two double bonds, e.g., linoleic acid, three double bonds, e.g., eleostearic acid, etc.

Within the scope of this invention, saturated fatty acid compounds are not useful. The mechanism requires fatty acid moiety unsaturation. Compositions containing mixtures of saturated and unsaturated fatty acid compounds, e.g., sodium morrhuate, should not be used due to the presence of a substantial amount of saturated fatty acid compounds. Sodium morrhuate is a mixture of the sodium salts of unsaturated and saturated fatty acids of cod liver oil.

Fatty acids which contain one or more hydroxyl groups (not containing the acid portion), e.g., dihydroxystearic acid and ricinoleic acid, are not useful within the scope of this invention. For example, the negative hydroxyl group in ricinoleic acid does not produce the necessary (cell) differentiation—this applies to all negative substituents on the main carbon chain. A high ammonia content is undesirable. These factors, plus degree of effectiveness, etc., are why the fatty acid compound should not be a substituted one. The fatty acid must not be cyclic. The fatty acid is preferably not branch chained. The fatty acid should be straight chained, with unsaturation at the center of the carbon chain.

The fatty acid compounds can be soaps such as the reaction product of fatty acids and organic basis—but such are not preferred compounds. The fatty acid compounds can be esterified fatty acids. The fatty compounds are most preferably a fatty acid salt. The fatty acid salts can be those prepared from metals such as, aluminum and alkaline earth metals, e.g., calcium, but are preferably those prepared by alkali metals, e.g., sodium (preferred), lithium, potassium, caseium and rubidium. (Ionic fatty acid compounds of sodium, such as, sodium oleate, are preferred even though the potassium salts are usually more soluble. Also, when the sodium balance becomes a factor, the sodium salts are the most preferred.) The metals can be used in the form of hydroxides, carbonates, etc. The fatty acid salts can be prepared from non-metallic inorganic bases, but such is not a preferred category of compounds.

The most preferred compound is sodium oleate.

Examples of useful compounds of oleic acid are: the methyl ester of cis-9-octadecenoic acid; ethyl ester of cis-9-octadecenoic acid; propyl ester of cis-9-octadecenoic acid; isopropyl ester of cis-9-octadecenoic acid; butyl ester of cis-9-octadecenoic acid; isobutyl ester of cis-9-octadecenoic acid; tert.-butyl ester of cis-9-octadecenoic acid; 3-methylbutyl ester of cis-9-octadecenoic acid; 2-methyl-2-butyl ester of cis-9-octadecenoic acid; phenyl ester of cis-9-octadecenoic acid; m-tolyl ester of cis-9-octadecenoic acid; p-phenylphenacyl ester of cis-9-octadecenoic acid; and the amide ester of cis-9-octadecenoic acid.

Examples of useful compounds of elaidic acid are: the methyl ester of trans-9-octadecenoic acid; the ethyl ester of trans-9-octadecenoic acid; and the amide ester of trans-9-octadecenoic acid.

Examples of useful octadecenoic acid compounds are: the methyl ester of trans-2-octadecenoic acid; the ethyl ester of trans-2-octadecenoic acid; the amide ester of trans-2-octadecenoic acid; the methyl ester of trans-3-octadecenoic acid; the methyl ester of cis-6-octadecenoic acid; the p-bromophenacyl ester of cis-6-octadecenoic acid; the amide of cis-6-octadecenoic acid; the triglyceride of cis-6-octadecenoic acid; the ethyl ester of trans-10-octadecenoic acid; the amide ester of trans-10-octadecenoic acid; the p-bromophenacyl ester of cis-11-octadecenoic acid; the methyl ester of trans-11-octadecenoic acid; the ethyl ester of cis-12-octadecenoic acid; and the methyl ester of trans-16-octadecenoic acid.

Examples of other useful monoethenoid fatty acid compounds are: the lithium salt of 9-heptadecenoic acid; the amide of 2-heptadecenoic acid; the methyl ester of 9-heptadecenoic acid; the ethyl ester of 9-heptadecenoic acid; the ethyl ester of 2-hexadecenoic acid; the methyl ester of 9-hexadecenoic acid; the ethyl ester of 9-hexadecenoic acid; the ethyl ester of 2-tetradecenoic acid; the methyl ester of 4-tetradecenoic acid; the ethyl ester of 4-tetradecenoic acid; the methyl ester of 9-tetradecenoic acid; the amide ester of 2-tridecenoic acid; the methyl ester of 12-tridecenoic acid; the ethyl ester of 12-tridecenoic acid; the amide of 7-dodecenoic acid; the ethyl ester of 11-dodecenoic acid; the methyl ester of 11-dodecenoic acid; the amide of 9-eicosenoic acid; the ethyl ester of 9-eicosenoic acid; the methyl ester of 11-eicosenaic acid; the amide of 2-undecenoic acid; the amide of 6-undecenoic acid; the ethyl ester of 9-undecenoic acid; the copper salt of 10-undecenoic acid; the ethyl ester of 10-undecenoic acid; the amide of 10-undecenoic acid; the amide of 2- decenoic acid; the methyl ester of 8-decenoic acid; the ethyl ester of 2-nonenoic acid; the ethyl ester of 8-nonenoic acid; the ethyl ester of 7-octenoic acid; the methyl ester of 7-octenoic acid; the amide of 2-octenoic acid; the methyl ester of 4-heptenoic acid; the methyl ester of 2-hexenoic acid; the ethyl ester of 2-hexenoic acid; the amide of 3-hexenoic acid; the methyl ester of 5-hexenoic acid; the ethyl ester of 2-pentenoic acid; and the amide of 15-tetracosenoic acid.

Examples of useful diethenoid fatty acid compounds having eighteen carbon atoms are: the methyl ester of 6:8-octadecadienoic acid; the methyl ester of 9:11-octadecadienoic acid; the ethyl ester of 9:11-octadecadienoic acid; the sodium salt of 9:12-octadecadienoic acid; the methyl ester of 9:12-octadecadienoic acid; the ethyl ester of 9:12-octadecadienoic acid; the amide of 9:12-octadecadienoic acid; the benzyl amide of 9:12-octadecadienoic acid; and the methyl ester of 10:12-octadecadienoic acid.

Examples of useful triethenoid fatty acid compounds having eighteen carbon atoms are: the methyl ester of 6:10:14-octadecatrienoic acid; the methyl ester of 9:11:13-octadecatrienoic acid; the ethyl ester of 9:11:13-octadecatrienoic acid; the methyl ester of 9:12:15-octadecatrienoic acid; the ethyl ester of 9:12:15-octadecatrienoic acid; and the methyl ester of 10:12:14-octadecatrienoic acid.

Examples of useful triple bond fatty acid compounds are: the methyl ester of 2-nonynoic acid; the methyl ester of 4-nonynoic acid; the methyl ester of 5-nonynoic acid; the methyl ester of 6-nonynoic acid; the methyl ester of 7-nonynoic acid; the methyl ester of 8-nonynoic acid; the amide of 2-nonynoic acid; the amide of 3-nonynoic acid; the amide of 4-nonynoic acid; the amide of 5-nonynoic acid; the methyl ester of 6-nonynoic acid; the amide of 7-nonynoic acid; and the amide of 8-nonynoic acid.

Most unsaturated fatty acids are found as the less stable cis isomers rather than the more stable trans isomer. The trans isomers have a double bond that is not in a readily accessable position (the two carbon chain portions protrude in opposite directions), and do not give anywhere as good as results. For this reason, elaidic acid (the trans isomer of the cis isomer, oleic acid) does not give anywhere as good results as does oleic acid.

Fatty acids (cis form) that have two or more double bonds are too reactive to perform in the preferred manner. An example of such is linoleic acid, which is too reactive, but is a cis form fatty acid, has two double bonds (somewhat centrally located) and has 18 carbon atoms.

Oleic acid which is $CH_3(CH_2)_7CH=CH(CH_2)_7COOH$, has a melting point of 13° C. Vaccenic acid, which is $CH_3(CH_2)_5CH=CH(CH_2)_9COOH$, has a melting point of 44° C. This illustrates another reason to have the double bond near the center of the carbon chain-generally such produces a lower melting point, which is important as a liquid fatty acid (salt) is then available over the normal range of usage of the liquefied composition.

The purity of the unsaturated fatty acid salt is important. A composition containing a high percentage of saturated fatty acid moieties will not be very effective. The preferred sodium oleate is particularily effective, while quite innoculous in a toxic and necrotic sense to human tissue.

The liquefied composition should contain between about 0.5 to 1 and about 10 percent by weight of the fatty acid salt and usually contains between 4 and 6 percent by weight of the fatty acid salt.

Examples of the liquid carrier for the non-necrotic fatty acid compounds are water (preferred), monoglycerides, diglycerides, etc. A mixture of water and ethanol is the most preferred liquid carrier; a salt (NaCl) can be added to make an isotonic aqueous solution as the liquid carrier.

The liquefied composition preferably contains a buffering agent, such as, sodium phosphate such as secondary sodium phosphate, sodium carbonate, or the salt of a weak organic acid with a strong base of which sodium citrate is an example. Examples of useful buffers are disodium hydrogen phosphate and sodium dihydrogen phosphate (preferred).

A buffer solution exerts control over large pH changes. The buffer capacity is directly proportional to the concentration of the buffer components. It is desirable to keep a high concentration of buffer components so that the pH does not shift during usage of the composition. To achieve this, the sodium oleate (or the like) should be present in a relatively high concentration so that the buffer components are present in a relatively high concentration.

In the preferred compositions using sodium oleate, the ethanol and phosphate buffer are pH level are believed to aid and complement the action of the sodium oleate in a slightly synergistic manner (and may provide the key to the extreme effectiveness of the most preferred composition).

An effective amount of ethanol, for example, ranges between 0.5 to 1 and 10 percent of ethanol. Higher levels of ethanol, such as up to 15 to 25 percent, can be used, but preferably no more than 10 percent of ethanol is used. (A somewhat rapid pH drift can occur if more than 10 percent of ethanol is used.)

Ethanol is a solubilizing agent for the sodium oleate, but the ethanol appears to also have a promoting effect or the like, on the sodium oleate activity. Other solubilizing agents could be used, but the total effectiveness would apparently not be anywhere near as great as when ethanol is used.

Preferably the liquefied composition comprises aqueous solution containing 4 to 6 percent of sodium oleate, 1 to 5 percent of ethanol, enough buffer to adjust the pH to 9.5 to 10.5, and the remainder distilled water. Preferably a phosphate buffer is used.

The most preferred liquefied composition comprises an aqueous solution containing 5 percent of sodium oleate, 5 percent of ethyl alcohol, enough sodium dihydrogen phosphate to adjust the pH to 9.8, and the remainder sterile distilled water.

If desired, in preparing the most preferred liquefied composition the pH can be raised to about 10 by the use of sodium hydroxide before the sodium oleate is added. Then the pH is raised back up to 9.8 by the addition of sodium dihydrogen phosphate, for example.

The composition used in the process of this invention can contain compatible, noninterfering additives. Any foam-causing agent (outside of the crucial basic ingredients) should be avoided for they tend to keep the liquefied composition away from the subject surface. Suitable preservations (for the liquefied composition) can be added in an amount not to exceed 0.5 percent by weight. No additives should be used which hinder the effectiveness of the composition of this invention.

The liquefied composition of this invention can be used in the form of a paste, gel, emulsion, or like by the addition of (an effective amount of) thickener to the liquefied composition. The thickener can be any suitable carrier or base material which forms a paste or the like. Useful thickeners are; methylcellulose; modified starches (5 to 40 percent by weight based on the total gel weight); polyvinyl alcohol (up to 7 percent by weight based on the total gel weight); gelatin (5 to 30 percent by weight based on the total gel weight); Carbowax; hydroxymethyl cellulose or hydroxyethyl cellulose or hydroxypropyl cellulose or methyl cellulose (2 to 20 percent by weight based on the total gel weight); glycerin (preferred); metallic salts of fatty acids (15 percent and above produces a gel); fatty acid esters (e.g., propylene glycol ethers of oleic acid); a water-miscible base made from propylene glycol, stearic acid, diglycol stearate and triethanolamine; glycerin and polyethylene glycol; water-dispersible glycol; water miscible base compound of propylene glycol, stearic acid, sorbitol, water and polyoxyethylene sorbitan monopalmitate; polyethylene glycols and propylene glycol cetyl alcohol, stearyl alcohol, spermacetic; polyoxyl 40 stearate; polyoxyl 8 stearate, water and glycerin; glycerin, cetyl alcohol, mineral oil, an ethoxylated fatty alcohol, water methylparaben and polyparaben. Useful thickeners which form thixotropic gels can be: sodium carboxymethylcellulose (0.5 to 25 percent by weight based on the total gel weight); and polyvinyl propylene (Pasdone C, made by GAF) (1 to 30 percent by weight based on the total gel weight. To form thixotropic gels, which art knows that certain concentrates of the gel base having a particular viscosity property or molecular weight need be used.

In general, the thickener, should be non-drying and water-miscible or water-soluble. The thickener can be an emulsifier. The thickener should be odorless, non-irritating and non-toxic. The thickener can be colorless or colored.

One advantage of the use of a thickener is that such helps minimizes the stability problems by suspending the chemical action. The thickner increases the shelf life of, for example, sodium oleate by slowing down the hydrolysis thereof.

The pertinent portions of copending application Ser. No. 961,932 entitled "Retardation of the Putrefaction of Hides and Skins", which was filed on Nov. 20, 1978, are incorporated herein. Such copending application discloses a process for the prevention and/or retardation of the putrefaction, spoilage or decay of skins, hides and/or pelts of animals. The process includes treating skins, hides and/or pelts which have not yet been tanned, tawed or otherwise similarly treated to produce leather, with an effective amount of a liquefied composition. The liquefied composition consists essentially of an effective amount of a non-necrotic sclerosing fatty acid salt, an effective amount of ethyl alcohol, a buffering agent and a water carrier. The fatty acid salt is one having been prepared from an unsaturated fatty acid having one double bond and from a alkali metal or an alkaline earth metal or an alkali metal compound or an alkaline earth metal compound. The liquefied composition has a pH between 9 and 11. The process utilizes, in part, the antimicrobial properties of the liquefied composition.

The pertinent portions of copending application Ser. No. 890,239, entitled "Injectable Solutions and Processes of Using Such", which was filed on Mar. 27, 1978, are incorporated therein.

The pertinent portions of copending application Ser. No. 918,795, entitled "Treatment of Sensitive Teeth Syndrome", which was filed on June 26, 1978, are incorporated herein.

The pertinent portions of copending application Ser. No. 918,817, entitled "Mouthwash and Method for Preventing and Removing Dental Plaque", which was filed on June 26, 1978, are incorporated herein.

The pertinent portions of copending application Ser. No. 927,614, entitled "Mouthwash and Method for Preventing and Removing Dental Plaque", which was filed on July 24, 1978, are incorporated herein.

The pertinent portions of copending application Ser. No. 929,119, entitled "Mouthwash and Method For Preventing and Removing Dental Plaque", which was filed on July 27, 1978, are incorporated herein.

The pertinent portions of copending application Ser. No. 918,792, entitled "Mouthwash and Methods", which was filed on June 26, 1978, are incorporated herein.

The pertinent portions of my copending and concurrently filed application entitled "Prevention or Retardation of Plant Diseases", which was filed on Dec. 1, 1978, are incorporated herein. Such copending application discloses a process for the prevention and/or retardation of plant diseases caused by fungi, mold, bacteria or virus. The surfaces of the plant (or at least the affected or diseased portion thereof) are treated with an effective amount of a solution. For treatment, the affected or diseased portion of the plant is treated with an effective liquefied composition. The solution contains 0.1 to 10 weight percent of a non-necrotic sclerosing fatty acid salt, an effective amount of ethanol, a buffering agent and a water carrier at a critical pH level. The fatty acid salt is one prepared from an unsaturated fatty acid having one double bond and from an alkali metal, alkaline earth metal, alkali metal compound or alkaline earth metal compound. The pH of the solution is controlled between 9 and 11. The process utilizes, in part, the antimicrobial properties of the liquefied composition.

The pertinent portions of my copending and concurrently filed application entitled "Retardation of the Spoilage of Foodstuffs", which was filed on Dec. 1, 1978, are incorporated herein. Such copending application discloses a method for the retardation of the spoilage of foodstuffs, such as, bananas, bread, meat, etc. The foodstuff is treated with an effective amount of a solution which contains an effective amount of a non-necrotic fatty acid salt, an effective amount of ethanol, a buffering agent and a water carrier. The fatty acid salt is one prepared from an unsaturated fatty acid having one double bond and from an alkali metal, alkaline earth metal, alkali metal compound or alkaline earth metal compound. The pH of the solution is between 9 and 11. The process utilizes, in part, the antimicrobial properties of the liquefied composition.

Fluorides used in dentrifices have delayed the formation of caries but cannot stop their formation. The fluorides, such as, stannous fluoride, fills (pseudo fill in) in the valleys and lesions in the teeth, which help prevent the plaque causing bacteria, etc., from attaching to the valley surfaces. The fluorides as such do not remove plaque (or prevent plaque formation in other areas of the teeth). The liquefied composition of this invention prevents the formation of dental plaque and removes the dental plaque bacteria. The use of fluorides causes minute cracks and lesions around fillings. The liquefied composition of this invention avoids that problem and apparently prevents the formation of such minute cracks and lesions.

Stannous fluoride fills in the cracks in the enamel, but does not strengthen the teeth. The liquefied composition of this invention will fill in the enamel cracks with new enamel, thereby strengthening the teeth by as much as five percent or more.

Abramovich and Sabelli, (J. Dent. Res. 53:94, 1974) incubated teeth with streptococcus mutans in vitro after a single topical application of stannous fluoride. They observed spherical bodies on the enamel surface under the scanning electron microscope and protection against enamel dosage. They were not certain whether the bodies were plaque remnants or hydroxyapatite and fluoride crystals. If what Abramovich and Sabelli did see was a bonding or esterification of the hydroxyapatite and sodium fluoride crystals, than such an ester could produce a sclerosing (fill in) effect which in fact could produce structural weakness of a tooth. (It has also been reported that fluoride, mostly not in ionic form, has been reported present in human plaque. High concentrations occur after topical application of fluoride and alter the diffusion-limiting properties of the plaque.) If a lesion was not present then this "filling" could act as a deterrent to the formation of caries merely by filling in architectural sites and crevices which would otherwise act as containers for thermal genesis and bacterial growth, however, if a lesion (gross or microscopic) was present on the tooth surface, periodontium or around a restoration sight, this "fill in" of hydroxyapatite and fluoride crystals would contribute to structural weakness and possibly to the reduction and/or improper collagen biosynthesis. The void is filled but not by a true union and therefore a minimum of trauma or torque produced by occlusal stress would tend to break down the ununited fibers around the edges of containment and the lesions would extend or diffuse. (The use of fluoride means that the negative hydroxyl group is present from the hydroxyapatite.)

A discussion of the theory of plaque formation, etc., is helpful as a background for this invention.

The initiation of the caries process is believed to be produced by the interplay of bacteria and a carbohydrate substrate in contact with a susceptible tooth surface. This interaction takes place within the dental plaque which is adherent to the tooth surface.

The first step is the deposition of a soft plaque on the tooth surface. Most of the plaque consists of dead and living bacterial surrounded by a gel-like organic matrix derived from the bacteria and saliva. Inorganic components from saliva and bacteria are also present within the plaque. It has been shown recently that the bacteria in the plaque utilizes sucrose to form extracellular dextran and levan which, together with salivary mucoprotein forms a "biological flue" that cements the bacteria and other particulate matter to the tooth surface.

The plaque appears as a whitish, glistening or dull mat on tooth surfaces. It is not soluble in water and acts as an effective diffusion barrier between the salivary buffers and the tooth surface. After ingesting sucrose, the pH of the plaque drops to about 5 and is maintained at that level for some time. This low pH probably produces the initial decalcification of the tooth surface in the process of caries development.

In the second phase, the plaque undergoes gradual calcification to form dental calculus. It is not known what initiates this calcification process. Bacteria must play a role in some way since conventional animals form much more calculus than their germ-free counterparts. When calcification of plaque occurs, it begins within and between the bacteria. Many foci of calcification begins within the plaque and with time, these foci coalesce.

Dental plaque or bacterial plaque is a mass of filamentous micoorganisms and large variety of smaller froms to the surface of a tooth; depending on bacterial activity and environmental factors, can give rise to caries, calculus, or inflammatory chancres in adjacent tissue. *Stedman's Medical Dictionary*, 20th Ed., (1961), p. 1174. Phage is an agent causing destruction or lysis of microorganisms (e.g., bacteria). Plaque is an area cleared by a phage in a bacterial growth; tache vierge. Kenneth, J. H., "A Dictionary of Biological Terms", 8th Ed., D. Van Nostrand Co., Inc., (1963). Dental calculus is (i) tartar or (ii) calcified deposits formed around the teeth. *Stedman's*, ibid., p. 249. Tartar is a brownish or yellow-brown deposit on the teeth, chiefly hydroxyapatite is an organic matrix. *Stedman's*, ibid., pp. 1483-84.

Dental caries is a localized, progressively destructive disease of the teeth that starts at the external surface (usually the enamel), with the apparent dissolution of the inorganic components by organic acids. These acids are produced in immediate proximity to the tooth by the enzymatic action of masses of microorganisms (in the bacterial plaque) on carbohydrates. The initial demineralization is followed by an enzymatic destruction of the protein matrix. Cavitation and direct bacterial invasion follow. In the dentin, demineralization of the walls of the tubules is followed by bacterial invasion and destruction of the organic matrix. Untreated dental carie progresses to the pulp, resulting in infection and its sequelae. *Stedman's ibid.*, p. 268.

Applicant believes that the lactrobacilli makes the sugar in food gram negative, so that the sugar can then affix to the ridges of the teeth. The bacteria are attached to the ridges of the teeth. The plaque formed is a gram negative material. The bacteria become pathogenic (negative) and attack the teeth.

It is noted that lactobacillic acid has the formula

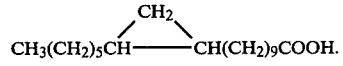

Oleic acid is a bent molecule:

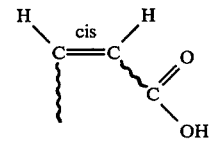

This configuration apparently presents the double bond in a symetric arrangement that has the right amount of reactivity, carbon chain length, double bond position, etc. The configuration of oleic acid and lactobacillic acid hint at the mechanism involved in this invention.

The composition of this invention does not disrupt or destroy the normal mouth microflowa, except for the plaque, and does not upset the digestive system (no diarrhea, etc., occurs if the mouthwash is consumed).

This invention includes the method of treating teeth for the prevention of caries or tooth decay by contacting the teeth with a sufficient and effective amount of the mouthwash to achieve the purpose. The plaque-forming bacteria are removed and kept from proliferating so that more plaque cannot be formed on the teeth. The removal, etc., of the plaque-forming bacteria results in the stoppage of plaque formation and its weakening and losening so it can easily be removed.

Another embodiment of this invention involves the method of treating and controlling gingivitis and related periodontal diseases of the gingival tissue. This embodiment is useful in preventing and treating of certain periodontal diseases, for example, inflammations of the gums such as, gingivitis and parulis, gingival retraction, receeding of the gum, such as, ulatrophy, etc. Gingivitis is inflammation of the gingival tissues. Types of gingivitis are a functional gingivitis, gingivitis marginal and cotton-roll gingivitis. By the treating and alleviating and curing periodontal diseases, such as, gingivitis, with the mouthwash of this invention, lose teeth are tightened with a return to healthy gums. The healthier gums, which have often receded down and away from teeth, frequently return to and near their original positions. Periodontitis, or pyorrhea, is a disease affecting the supporting tissues of the teeth including the gingiva, and membrane lining the sockets where the teeth lie, and the bones surrounding the teeth. The disease may initially be associated with conditions of constant irritation of the gingiva by dental calculus, food impaction, poor dental restorations, traumatic occlusion or chemical irritants.

The gums may be seriously harmed by deposits of dental calculus (tartar), a combination of minerals and bacteria found in the mouth. The bacterial associated with tartar can secrete enzymes and endotoxins which can irritate the gums and cause an inflammatory gingivitis. As the gums become increasingly irritated by this process they have a tendency to bleed, lose their toughness and resiliency, and separate from the teeth, leaving periodontal pockets in which debris, secretions, more bacteria and toxins further accumulate. It is also possible for food to accumulate in these pockets, thereby providing nourishment for increased growth of bacteria and production of endotoxins and destructive enzymes. The pus that forms in this process is capable of destroying gum and bone tissue. A variety of bacteria are generally found to be present during the active stages of periodontal disease. Such organism as streptocci, staphylococci, pneumococci, etc., are usually present, and are found in the purulent discharge as well as in the involved tissue, and may be absorbed into the general system through the lymphatics or venous blood stream.

The progression of the pyorrheic process usually begins with gingivitis, initiating at the margins of the gums, in which the gingiva become more tender and sensitivie, and appear flabby, inflammed and swollen. Periodontal pockets become apparent, and infection takes place in these pockets. Because the periodontal pockets cannot be cleaned by brushing or the use of dental floss, infection becomes progressive and constant. Due to, among other things, the effect of the liquefied composition of this invention has on the microorganism causing the invention, etc., in these advanced disease stages the mouthwash can cure and alleviate such advanced periodontal diseases. The adhesion and readhesion of the microbes is prevented or retarded, and attached microbes are detached.

Due to the effect that the liquefied composition of this invention has on microorganisms, the liquefied composition can be used to eliminate "bad breath" while removing and preventing bad breath.

The liquefied composition of this invention can be used as a deodorant. It can be directly applied as a liquid, or can be placed on an absorbent pad or the like and applied in liquid form by putting on the affected surface. Adhesion of microbes which directly or indirectly cause body odors is prevented or retarded, and such microbes are detached.

Sinusitis is an inflammation of a sinus. The condition may be purulent or nonpurlent, acute or chronic. Depending on the site of involvement it is known as ethmoid, forntal, maxillary, or sphenoid sinusitis. The etiology of sinusitis must be regarded as one of an inborn cellular weakness and susceptibility to microbes being able to attach and proliferate within the confines of the nasal cavities. The threshold or below threshold properties of the immune systems ability to combat said proliferations constitutes whether the patient is chronic or acute, purulent or non-purulent. The horrendous combinations of inborn errors of metabolism seems pointless to theorize upon as regardless of what hypo or hyper combinations exist—the end result remains the same. The theory that the cellular ionic concentration pattern which is produced by the normal electrical potential existing across the surface membrane acts to exert precise control over division of body cells has been developed.

It is logical to accept the theory that cohesion or the molecular attraction of bacterium could be directed by the ionic field. As it is attracted and attached it could also be detached by rearrangement of the bio-electrical field. This action is rapid and separate from the immune system. The immune system must "kill" to detach whereby the ionic system detaches by depolarization.

To date the treatment of sinusitis and related syndromes has been on primarily of various combinations of antihistamines and decongestants which have proven effective to a degree, however, these proucts have many contraindications as well as adverse side effects. (About one person in four will experience some bothersome reaction during treatment with a given antihistamine.)

The ability of the liquefied composition of this invention to retard the adhesion of microbes, and to cause their detachment, means it can be used to treat or prevent sinustis.

One embodiment of this invention involves the treatment and healing of "the dry socket syndrome", which is localized osteomyelitis of the alveolar crypt in the maxilla and/or the mandible. This is done by the use of one of the compositions of this invention containing a non-necrotic vascular sclerosing fatty acid compound.

Perhaps more importantly, this invention involves the prevention of "the dry socket syndrome". The prevention can be carried out by placing a composition containing a non-necrotic vascular sclerosing fatty acid compound directly into the extraction site immediately following extraction of the tooth.

The (injectable) liquefied compositions described herein can be used, but preferably the creams described herein are used. Even more preferably, a non-water-soluble or non-water-miscible cream base is used in the cream or as a protective cover for the water-miscible or water-soluble cream. Any suitable non-water-soluble or non-water-miscible cream base can be used, but the preferred one is a mixture of petroleum and lanolin—such cream bases are described in more detail below.

A dry socket is a condition which occurs after tooth extraction, resulting in exposure of bone with localized osteomyelitis of an alveolar crypt, and symptoms of severe pain. Osteomyelitis is inflammation of bone caused by a pyrogenic organism. It may remain localized or it may spread through the bone to involve the marrow cortex, cancellous tissue and periosteum.

Inasmuch as the actual pulling and tearing mechanism employed during extraction dictates that minute fragmenting of the periosteum and bone must occur, applicant can then postulate that the same pathological changes follow as do show a fracture, per se, occurs. At this tramatic time some cells are completely destroyed—others are damaged. When part of a cell is damaged, transmembrane resting potential at this area may be zero and permeability to ions may be very high. It has been said that perhaps the remaining part of the cells, with raised metabolic activity, can continue to sustain ionic separations despite the loss through the injured area. This cellular area condition, rather it be completely destroyed or moderately damaged, would produce an injury current (pain). The direction of the current is such that the damaged area appears as a source of negative charge. The violent pull at the time of extraction would tend to create some hematomas, clots and a "broken field" (bioelectric) current flow. Such alteration could then become a cesspool whereby the pyogenic organism could readily functon osteomyelitis). By applying a composition containing a non-necrotic vascular sclerosing fatty acid compound directly following extraction, the following will occur: (1) clots, per se, will not form in such concentrated bioelectrical fields; (2) the electrical current flow could be more stabilized; and (3) a more stabilized pH. This major stabilizing at the time of trauma has a tendency to produce a more ideal field, for an osteogenic conversion of selected cell function—thus sealing the cavity and lessening the changes of the seating of pyogenic organisms.

"The dry socket syndrome" is very much the same condition which, for example, would occur during surgery of the caprus. A different bone and a different initial exposure (pulling or tearing is opposed to cutting) is involved, but the fact remains that the ensuing cellular changes remain pretty much the same.

Another embodiment of this invention involves the use of a liquefied composition comprised of a non-necrotic vascular sclerosing fatty acid compound and a liquid carrier or a cream containing a non-necrotic vascular sclerosing fatty acid compound and a carrier for the treatment of bone, including the periosteum which has been cut, or otherwise penetrated during open reduction surgery. After the surgery, the material containing the non-necrotic vascular sclerosing fatty acid compound is applied to the bone area which is cut or the like. (This should be done even if no visible cuts or the like are seen, as mosaic cuts or the like may be present.) A rapid healing of the bone cut or like occurs, faster than if the bone cut or like was not treated (left to natural healing). The use of the composition of this invention lessens infection at the time of the "open reduction" surgery—see the above discussion of "the dry socket syndrome".

If a liquefied composition (using say a water carrier) is used, it can be used as a foam or a spray.

The term liquefied composition includes a cream.

A cream is preferred in some instances, and a thioxtropic gel is most preferred. A cream has a number of advantages and disadvantages which have been discussed above.

This embodiment also applies to open reduction of a fractured bone. The above discussion applies to this feature of this embodiment.

In general, the gel carrier should be non-drying and water-miscible or water-soluble. The gel carrier can be an emulsifier. The gel carrier should be odorless, non-irritating and non-toxic. The gel carrier can be colorless or colored.

The gel can be used in suppository form or the like where it is necessary to leave the incision or cut open (or to reopen periodically). Such suppository-like units can contain a cream, for example, made from lactose, polyethylene glycol 400, polysorbate 80, polyethylene glycol 4000 and glycerin, or which is a water-soluble base of polyethylene glycol and polyoxyethylene palmitate, or which is cocoa butter.

The gel can be applied as an aerosal-spray. The basic gel carrier could be isopropyl myristate with an inert propellant mixture of trichloromonfluoromethane and dichlorodifluoromethane.

The gel can be applied as a foam. A suitable water-miscible foaming agent can be used.

In certain instances, for example, in the treatment of "dry sockets", it is desirable to use a cream or gel which comes in contact with moving body fluids or outside fluids or solids (such as, water and food). Such gel bases generally should be non-drying, should not disintegrate or liquefy at body temperature and should not be washed away by things such as mouth fluids. Such gel bases should not be water-miscible or water-soluble.

Another embodiment of this invention involves the method of contacting a body cavity, the gastrointestinal canal, the urinary canel or the like with an effective amount of a liquefied composition which prevent infection from occuring and the growth of pathogenic microorganisms. The liquefied composition contains an effective amount of a non-necrotic fatty acid compound prepared from an unsubstituted, unsaturated fatty acid having at least one double bond, a liquid carrier, an effective amount of a buffering agent and an effective amount of ethanol. The pH of the liquefied composition is between 8 and 11. The disclosure on the mouthwash components, etc., applies here. The most preferred method involves the use of a liquefied composition which contains about 5 percent of sodium oleate, about 1.5 percent of ethanol, enough disodium hydrogen phosphate to adjust the pH to about 9.8 and the remainder water.

The liquefied composition can be used for its "germ fighting qualities".

The liquefied compositions of this invention can be used in any flesh incision or the like. The liquefied composition prevents (or helps) infection of the tissue incision, even after suturing or other closing off of the incision.

For surgical work, as little as 0.5 percent by weight of sodium oleate can be used, but higher percentages are preferred.

The liquid composition of this invention can be used when and after medical probing devices have been inserted into the various body cavities and tracts.

The liquid composition of this invention apparently renders various microorganisms, e.g., Streptococci, non-pathogenic by an electrolytic type of action. The microorganisms are prevented from becoming polarized in massive groupings—the liquid composition causes a dispersion of the microorganisms in the body fluids, which keeps them from becoming pathogenic. The mechanism may be that the liquid composition prevents or inhibits the microorganisms from producing toxins. The microorganisms are prevented from becoming morbidly pathogenic.

The plaque forming bacteria in the mouth stick to the ridges of the teeth. It thought that the liquified composition of this invention achieves plaque formation prevention by not allowing such bacteria to seat and become pathogenic. The liquified composition does not open up the enamel to attack by stripping of any protective, non-plaque, non-calculus material from the face of the teeth.

The liquid composition of this invention is not systemic acting. The liquified composition of this invention is not bacteriostatic or bacteracidal or antibacterial or the like, in the normal sense of such terms. The liquid composition apparently keeps the microorganisms from attaching (or brings about a reduction in the microorganisms population).

The diseases, infections, or maladies casued or aggrevated by bacteria or other microbes are prevented, retarded or lessened by the antimicrobial properties of the composition used in the invention.

The process of this invention is also useful to coat implants (e.g., hip replacements, bone implants, teeth implants, etc.), to enhance wound healing (reducing and preventing microbial infection), to treat dermatosis and itching caused by microbes, to coat first-aid prodcuts (e.g., gauze pads, band-aids, etc.), in surgical washes and scrubbings, to treat athlete's feet, in cosmetic preparation (e.g., base lotion, eye mascara, etc.), wash the tops of butcher blocks, food and meat cases, food counters and the like, to treat cuts, scratches and the like, as an eye wash, to clean contact lenses, as a bladder flush, as a douche to treat candidiasis and similar microbial infections, shaving creams, hand creams, and after shave lotions, in suppositories, on medical probing devices, in aerosal sprays, on sutures, in a liquid dentrfrice, to treat cold sores, as a disinfectant, to treat gastrointestinal microbial infections and in shampoos.

GRADIENT HYDROGEN THEORY

The cellular ionic concentration pattern which is produced by the normal electrical potential existing across the surface membrane acts to exert precise control over division of body cells. This theory has been developed and experimentally verified in tests with mammalian cells.

Applicant postulates that the prevention of the synthesis of DNA could well be completely blocked by highly negative charges created by a halo of containment of hydrogen. Factors leading to the bio-electric imbalance of the cell could be triggered by chill-factor, stress, chemicals, viruses, bacterium, radiation, etc. The ultimate configuration produced, however, would for the most part remain the same.

To simply illustrate the basic configuration of the Alpha state, applicant uses the rapid effect of ionization upon a predisposed passenger in an air-conditioned auto. The passenger is one who is highly susceptible to chill factors. The chilling as well as the falling of the barometric pressure could produce a constriction of the minute blood vessels in the lining of the nasal and throat cavity (vasoconstriction). The contraction of blood vessels would shrink the mucous membrane of the nose and throat thus reducing the adhesive qualities of the cell surface. These environmental conditions could alter the hydrogen ion concentration permitting it to trap, with a halo of containment, mucous cells and the stop thus immune systems to respond. The halo of containment would create an Alpha phase and quickly allow the bacteria to feed and proliferate. Thus the passenger would suffer the pain and discomfort associated with the common cold and sore throat syndrome. Once the passenger leaves the confines of this man-made environment and returns to a warmer, more balanced ionic field the symptoms quickly reverse and the congested nasal passages and sore throat syndrome quickly disappears. "Nature does not indulge in luxuries," therefore, the body's responses have quickly demonstrated their ionic dependency and that the Alpha and Beta states can in essence be triggered by the response of the hydrogen concentration to the bio-electric field.

Applicant now considers the lift of the halo of containment produced in the oral cavity. This condition would not be a result of chill factor or barometric pressure but would rest entirely on the hydrogen ion concentration resulting from the intake of carbohydrates responding to the inborn errors of metabolism. Basically the same cellular configuration would occur and again the Alpha state would allow the bacteria to feed and proliferate. This also occurs on the surface of plaque thus producing a "coral" bacterial structure. The "releasing" of the bacterial structure would in essence reduce the adhesive qualities of plaque and would tend to minimize the mechanical removal.

Sensitivity or the failure to produce odontoblasts again relates to the basic concept. Here the failure of the cell to differentiate could occur from occlusional trauma, metabolic imbalance or architectural vacuums . . . this condition, however, is void of bacteria. To designate or differentiate the heterogeneous responses which triggers all mechanisms would be presumptuous on the applicant's part. The applicant has concentrated and postulated on the obvious results rather than the intricate synergestic causes, however, the basic configuration leading to alteration is duplicated by nature rather it be soft tissue, bone or teeth. The development of expansion and sometimes spiculation must therefore be triggered and/or controlled by the ionic concentration of hydrogen.

Unless otherwise stated or indicated, in the following examples and throughout this specification, all percentages, parts and proportions are expressed on a weight basis.

The following examples further illustrate, but do not limit this invention.

EXAMPLE 1

A liquefied composition containing 5 weight percent of sodium oleate, 5 weight percent of ethanol, enough sodium dihydrogen phosphate to obtain a pH of 9.8, 0.1 weight percent of sodium oleate and the remainder sterile distilled water (q.s.). The liquefied composition was placed in amber glass bottles.

An identical liquefied composition, but containing 5 weight percent of sodium oleate, was prepared and bottled.

A further identical liquefied composition, but containing 10 weight percent of sodium oleate, was prepared and bottled.

EXAMPLE 2

The 5 percent sodium oleate solution of Example 1 was used in the following manner to investigate the antimicrobial profile and properties of the sodium oleate composition at pH 9.8.

The test procedure used composed of inoculating liquid cultures of various bacteria and molds with different amounts of sodium oleate solution. Two of the microbe and oleate solutions were adjusted to pH levels of 7 and 9 (which were used along with the solution having a pH of 9.8). The liquid cultures were then incubated at body temperature. The cultures were observed at 24 hours in order to determine whether or not the bacteria had grown. Results were recorded for growth, partial growth and no growth. The following microbial species were used in the experiments:

(i) *Candida albicans*
(ii) *Streptococous salivarius* and *sanguis*
(iii) *Actinomyces viscosus*
(iv) *Bacteroides metruchia*

A problem that occurred during these trials was a persistent turbidity of the test cultures. It appears that sodium oleate reacts with or is precipitated by the culture medium used (trypticase soy broth) to produce a highly cloudy solution. This occurred particularly at the lower pH's used.

Because of the clouding problem, the results of testing sodium oleate were considered valid only for the solution at pH 9.8. The results are presented in Table I:

TABLE I

Antimicrobial Effectiveness of the Sodium Oleate Composition at pH 9.8

| Microorganism | Sodium Oleate Concentration (ml of 5% solution) | Results[1] |
|---|---|---|
| Candida albicans | 5.0 | − |
|  | 2.5 | − |
|  | 0.5 | + |
|  | 0 | + |
| Streptococcus salivarius and sanguis | 5.0 | − |
|  | 2.5 | − |
|  | 0.5 | − |
|  | 0 | + |
| Actinomyces viscosus | 5.0 | − |
|  | 2.5 | − |
|  | 0.5 | − |
|  | 0 | + |
| Bacteroides metruchia | 5.0 | − |
|  | 2.5 | − |
|  | 0.5 | + |
|  | 0 | + |

Note:
[1] − means no growth of the microorganism
+/− means minimal growth of the microorganism
+ means heavy (good) growth of the microorganism Table 1 shows that sodium oleate (in the formulation of this invention) has antibacterial activity against all of the above bacterial fungal species. The two tested species, C. albicans and B. matruchlia were inhibited by the 2.5 and 5.0 percent dosages of sodium oleate used, but were unaffected by the lower dosage of 0.5 percent. This suggests a threshold or dose-related effect upon some bacterial and mold species.

These results show a pattern of antibacterial and antifungal activity of sodium oleate.

A pH of 9.8 appears to be the optimum pH of the sodium oleate composition re antimicrobial activity.

EXAMPLE 3

A liquefied composition containing 5 weight percent of sodium oleate, 1.5 weight percent of ethanol, enough sodium dihydrogen phosphate to obtain a pH of 9.8 and the remainder sterile distilled water (q.s.). The liquefied composition was placed in 16 ounce (amber) bottles.

EXAMPLE 4

A Streptococcus equi culture received from ATCC in deactivated dried ampule form. The dried ampule of Streptococcus equi was activated with ½ cc sterile milk at 100° F. The Streptococcus equi was streaked via sterile swab onto two sheep blood agar plates. Plate N was streaked after addition of 5 cc. of sterile saline to the activated Streptococcus equi at the same time. Plate O was streaked after addition of 5 cc of sterile saline and 1 cc of the liquefied composition (5 percent) of Example 3 was mixed with the activated Streptococcus equi for 2 minutes. The plates were placed in the incubator for 48 hours at 100° F. Plate N had good growth after 48 hours and plate O had no growth.

Then a swab of activated Streptococcus equi was placed in 2 cc of sterile saline for 2 minutes and than placed on sheep blood agar plate A. A swab of activated Streptococcus equi was placed in 2 cc of the liquefied composition (5 percent) of Example 3 for 2 minutes and then placed on a sheep blood agar plate B. The plates were placed in the incubator for 48 hours at 100° F. Plate A had good growth after 48 hours and plate B had no growth.

This shows that the liquefied composition of this invention is effective against gram positive bacteria. (In this field, the liquefied composition, of Example 3 is just as effective at full strength as at a 5:1 water to liquefied composition dilution.)

EXAMPLE 5

The first test of Example 4 was repeated using Streptococcus pyogenes. The dilution factor was the same, but the microorganism was only heated at 100° F. at 24 hrs. There was no growth on the invention treated plate, but there was heavy growth on the untreated plate. It is believed that the invention composition keeps the microorganism cells from proliferating and adhering.

EXAMPLE 6

The two tests of Example 4 was used against *Ps. aeruginosa*, Salmonella sp. 24, Salmonella sp. 21, *S. agalactine, S. dysgalactiae, S. lactis, S. aureus str.* 1, *S. aureus str.* 2, and Proteus sp. At both levels, the result was that there was a "pacification" of the various bacteria species—there was no growth or inhibition (reduction) of the species, but there was a placing of the microorganisms in a kind of limbo where they could not grow or become pathogenic.

EXAMPLE 7

Before the flesh in the open reduction of a fractured dog leg was sutured up, a cream was applied to the open bone surface and into the open bone fracture site. The cream (a colloidal suspension) contained 5 percent by weight of sodium oleate, 0.1 percent by weight of sodium phosphate (monobasic, monohydrate, 1.5 percent by weight of ethanol, 5 percent by weight of methylcellulose (60 HG 4000 cps) enough sodium hydroxide to obtain a pH of 9.8 and the remainder purified water (q.s.). The suturing was completed. The fracture was substantially cured in a rapid time, faster than by natural healing.

EXAMPLE 8

An injectable liquefied composition containing 5 weight percent of sodium oleate, 1.5 weight percent of ethanol, enough sodium dihydrogen phosphate to obtain a pH of 9.8 and 50 ml. of sterile distilled water (q.s.).

A gelding having bone chips around a fractured leg site was operated on to remove the bone chips. The actual fracture site was injected with such liquefied composition, and the surrounding area was sprayed with such liquefied composition. The incision was sutured up in a normal manner. The fracture healed more rapidly than if natural healing had been allowed to occur, and no infection developed in the open reduction surgery site or incision.

EXAMPLE 9

Example 8 was repeated, except that the cream of Example 7 (instead of the liquefied composition of Example 8) was inserted into the fracture site and applied to the surrounding area. Slightly more rapid healing occured and no infection developed in the open reduction surgery site or incision.

EXAMPLE 10

A tooth was extracted. Immediately after the extraction, the liquefied composition of Example 8 was placed in the extraction site (bone and tissue). No infection set in and no "dry socket syndrome" developed at the extraction site.

EXAMPLE 11

Example 10 was repeated, except that the cream of Example 7 was used instead of the liquefied composition of Example 8. No infection set in and no "dry socket syndrome" developed at the extraction site.

EXAMPLE 12

A liquefied composition containing 2.5 weight percent of sodium oleate, 5 weight percent of ethanol, enough sodium dihydrogen phosphate to obtain a pH of 9.8 and the remainder sterile distilled water (q.s.). An identical liquefied composition, but containing 5 weight percent of sodium oleate, and another identified liquefied composition, but containing 10 weight percent of sodium oleate, were prepared. Each of the liquefied compositions were placed in glass bottles.

The untreated, scrapped hide of a freshly slaughtered cow was cut into 4 equal parts. The first part of the hide was the control and was untreated. The second part of the hide was treated with the liquefied composition containing 2.5 weight percent of sodium oleate. The third part of the hide was treated with the liquefied composition containing 5 weight percent of sodium oleate. The fourth part of the hide was treated with the liquefied composition containing 10 weight percent of sodium oleate. The four treated pieces of hide were kept in a room at room temperature.

The hair was easily pulled out of the control piece of hide in 24 to 36 hours after the experiment started. The flesh of the control piece of hide deteriorated (became putrefied with a strong odor of putrefaction) after 2 days. The piece of hide treated with the liquefied composition containing 10 weight percent of sodium oleate was only about the same as the control. That is, the hair was easily pulled out after 24 to 36 hours and the (fourth) piece of hide putrefied after about 2 days. The second piece of hide (treated with the liquefied composition containing 2.5 weight percent of sodium oleate) had the following results: the hair was easily pulled out after 48 to 72 hours; and the piece of hide putrefied after about 3 days. With the third piece of hide (treated with the liquefied composition containing 5 weight percent of sodium oleate), the hair was still intact in the hide at the end of the sixth day, ⅔ths of the hair was intact at the end of the seventh day and the hide did not putrefy until after the seventh day. Based on this data, a range of 3.5 to 9 weight percent of sodium oleate was chosen. Early in the test the hide thickness (hair, etc.) of about ½ inch had diminished substantially for all but the 5 percent-treated piece of hide.

EXAMPLE 13

A liquefied composition containing 5 weight percent of sodium oleate, 5 weight percent of ethanol, enough sodium dihydrogen phosphate to obtain a pH of 9.8, 0.1 weight percent of sodium benzoate, and the remainder sterile distilled water (q.s.). The liquefied composition (termed GHT 7701) was placed in amber glass bottles.

A placebo was prepared which had the same composition as GHT 7701, except that the 5 weight percent of sodium oleate was left out. The placebo (termed GHT 7703) was placed in amber glass bottles.

GHTY 2.5 is the 2.5 weight percent sodium oleate solution of Example 1; GHTY 5 is the 5 weight percent sodium oleate solution of Exmaple 1; and GHTY 10 is the 10 weight percent sodium oleate solution of Example 1.

The following test organisms:

| | |
|---|---|
| *S. aureus* | ATCC #6538 |
| *Ps. aeruginosa* | ATCC #9027 |
| *E. coli* | ATCC #8739 |
| *C. albicans* | ATCC #10231 | were grown on T-Soy agar slants. The 24 hour growths were removed with sterile isotonic saline. Serial dilutions of each suspension were made and plated to obtain colony levels. (Tubes were immediately iced to prevent further bacterial growth.) These cultures were then diluted to yield 240,000,000/ml. Equal quantities of the standardized cultures were then blended.

A 20 gram portion of each sample for test was transferred to sterile screw-cap jars. 0.1 ml of the mixed cultures was added to each and thoroughly blended to homogeneity. This yielded an inoculation of 1,200,000/g of product.

Within 15 minutes of the time of inoculation, 1 gram portions were weighted into sterile buffered Tween 80-Azolectin water blanks from which serial dilutions were made for plating. The remainder of the inoculated material, in tightly sealed jars, were stored at 70° to 72° F. for further analyses. One week later and at weekly intervals for a total of four weeks, the samples were again plated.

The counts obtained are detailed below:

TABLE II

| Sample Identification | Plate Counts Per Gram | | | | |
|---|---|---|---|---|---|
| | Initial | After 1 wk. | After 2 wks. | After 3 wks. | After 4 wks. |
| GHTY 2.5 | 1,200,000 | 8,000,000 | 71,000,000 | 49,000,000 | 880,000 |
| GHTY 5 | 280,000 | <10 | <10 | <10 | <10 |
| GHTY 10 | 230,000 | <10 | <10 | <10 | <10 |
| GHT 7701 | 420,000 | <10 | <10 | <10 | <10 |
| GHT 7703 | 1,200,000 | <10 | <10 | <10 | <10 |
| Inoculated Isotonic Salt Control | 1,200,000 | | | | |

Note: < = Less than

EXAMPLE 14

The five test solutions of Example 13 were used herein.

The test organism was *Aspergillus niger* ATCC # 16404.

A slant of *Asperigillus niger* was transferred to the hardened surface of Sabouraud Dextrose Agar in a Roux flask and incubated at 32° C. After 7 days growth, the mold spores were harvested. Mycelia were filtered out through sterile filters and the spores concentrated by centrifuging. They were washed with sterile saline, recentrifuged and dispersed in saline. This mixture was then pasteurized at 55° C. for 10 minutes (to destroy Mycelia) and a portion plated at serial dilutions to determine the spore level. (The spore dispersion was immediately iced to prevent further growth.) Once the organism level was established, it was standarized with saline to yield a count of 20,000,000 per ml.

A 20 gram portion of each sample for test was transferred to sterile screw-cap jars. 0.1 ml of the mold culture was added to each and thoroughly blended to homogenetiy. This yielded an inoculation of 100,000 spores per gram of product.

Within 15 minutes of the time of inoculation, 1 gram portions were weighed into sterile buffered Tween 80-Azolectin water blanks from which serial dilutions were made for planting. The remainder of the inoculated material, in tightly sealed jars, were stored at 70° to 72° F. for further analyses.

One week later and at weekly intervals for a total of four weeks, the samples were again plated.

The counts obtained are detailed below:

TABLE III

| Sample Identification | Plates Counts per Gram | | | | |
|---|---|---|---|---|---|
| | Initial | After 1 wk. | After 2 wks. | After 3 wks. | After 4 wks. |
| GHTY | 100,000 | 360,000 | 480,000 | 190,000 | 460,000 |
| GHTY 5 | 100,000 | 140,000 | 40,000 | 99,000 | 35,000 |
| GHTY 10 | 100,000 | 30,000 | 10,000 | 1,600 | 130 |
| GHT 7701 | 100,000 | 1,800 | <10 | <10 | <10 |
| GHT 7703 | 100,000 | 20 | 10. | <10 | <10 |
| Inoculated Isotonic Salt Control | 100,000 | | | | |

Note: < = Less than

What is claimed is:

1. Process for preventing microorganisms from attaching or reattaching to a surface which comprises treating the microorganisms or the surface or both with an amount of a liquefied composition effective to prevent said attachment or reattachment of said microorganisms, said liquefied composition consisting essentially of an effective amount of a non-necrotic sclerosing fatt6y acid salt which prevents said attachment or reattachment of said microorganisms, ethyl alcohol in an amount of about 0.5 to about 10 percent, a buffering agent and a water carrier, said salt containing an unsaturated fatty acid having one double bond moiety and containing an alkali metal or an alkaline earth metal, said fatty acid salt having 14 to 22 carbon atoms, and said liquefied composition having a pH between 9 and 11, said buffer being used in an amount sufficient to maintain said pH range, whereby the microorganism is prevented or retarded from attaching or reattaching to the surface.

2. Process as claimed in claim 2 wherein the pH of the liquefied composition is between 9.5 and 10.5.

3. The process as claimed in claim 2 wherein the microorganism is bacteria or mold.

4. The process as claimed in claim 2 wherein a thickner is present in the liquefied composition.

5. The process as claimed in claim 2 wherein the fatty acid salt contains 14 to 22 carbon atoms, and the liquefied composition contains 0.1 to 5 percent ethanol.

6. The process as claimed in claim 2 wherein the liquefied composition is comprised of sodium oleate, water, ethanol and sodium dihydrogen phosphate.

7. The process as claimed in claim 2 wherein the treatment step is repeated.

8. The process as claimed in claim 2 wherein said salt has been prepared from an unsaturated fatty acid having one double bond and from an alkali metal or an alkaline earth metal or an alkali metal compound or an alkaline earth metal compound.

9. The process as claimed in claim 8 wherein said alkali metal compound is a carbonate or a hydroxide.

10. The process as claimed in claim 8 wherein said alkaline metal compound is a carbonate or a hydroxide.

11. Process for detaching microorganisms attached to a surface which comprises treating the surface or the microorganisms attached to the surface or both with an amount of a liquefied composition effective to cause said detachment said microorganism, said liquefied composition consisting essentially of an amount of a non-necrotic sclerosing fatty acid salt, which causes said detachment of said microorganisms, ethyl alcohol, in an amount of about 0.5 to about 10 percent, an effective amount of a buffering agent and a water carrier, said salt containing an unsaturated fatty acid having one double bond moiety and an alkali metal or an alkaline earth metal, said fatty acid salt having 14 to 22 carbon atoms, and said liquefied composition having a pH between 9 and 11, said buffer being used in a range sufficient to maintain said pH range, whereby the microorganism is detached from the surface and prevented from proliferating on or near the surface.

12. Process as claimed in claim 11 wherein the pH of the liquefied composition is between 9.5 and 10.5.

13. The process as claimed in claim 11 wherein the fatty acid compound is sodium oleate.

14. The process as claimed in claim 11 wherein the microorganism is bacteria or mold.

15. The process as claimed in claim 11 wherein a thickner is present in the liquefied composition.

16. The process as claimed in claim 11 wherein the fatty acid salt contains 14 to 22 carbon atoms, and the liquefied composition contains 0.1 to 5 percent ethanol.

17. The process as claimed in claim 11 wherein the liquefied composition is comprised of sodium oleate, water, ethanol and sodium dihydrogen phosphate.

18. The process as claimed in claim 11 wherein the treatment step is repeated.

* * * * *